(12) United States Patent
Takeshita et al.

(10) Patent No.: US 7,041,714 B2
(45) Date of Patent: May 9, 2006

(54) DENTAL ADHESIVE

(75) Inventors: Hiroshi Takeshita, Tokyo (JP); Emi Ishida, Tokyo (JP); Hideki Kazama, Tokyo (JP)

(73) Assignees: Tokuyama Corporation, Yamaguchi (JP); Tokuyama Dental Corporation, Tokyo (JP)

( * ) Notice: Subject to any disclaimer, the term of this patent is extended or adjusted under 35 U.S.C. 154(b) by 286 days.

(21) Appl. No.: 10/467,862

(22) PCT Filed: Oct. 7, 2002

(86) PCT No.: PCT/JP02/10412

§ 371 (c)(1),
(2), (4) Date: Aug. 13, 2003

(87) PCT Pub. No.: WO03/057180

PCT Pub. Date: Jul. 17, 2003

(65) Prior Publication Data

US 2004/0077746 A1     Apr. 22, 2004

(30) Foreign Application Priority Data

Dec. 28, 2001   (JP)   .............................. 2001-399569

(51) Int. Cl.
*A61K 6/83*   (2006.01)
*A61C 5/00*   (2006.01)

(52) U.S. Cl. ..................... 523/118; 523/116; 433/228.1
(58) Field of Classification Search ................ 523/118, 523/116; 433/228.1
See application file for complete search history.

(56) References Cited

U.S. PATENT DOCUMENTS

| 4,612,384 A | * | 9/1986 | Omura et al. ................ 558/198 |
| 6,583,197 B1 | * | 6/2003 | Wada et al. ................... 522/84 |
| 2002/0198284 A1 | * | 12/2002 | Nakatsuka et al. ......... 523/116 |

FOREIGN PATENT DOCUMENTS

| JP | 63216811 A | | 9/1988 |
| JP | 09067222 A | | 3/1997 |
| JP | 11071220 A | * | 3/1999 |

* cited by examiner

*Primary Examiner*—Tae H. Yoon
(74) *Attorney, Agent, or Firm*—Sherman & Associates (57) ABSTRACT

A dental adhesive containing an acidic group-containing radically polymerizable monomer, a non-acidic radically polymerizable monomer, a chemical polymerization initiator and a filler, as well as a 2,4-diphenyl-4-methyl-1-pentene. When the dental adhesive is used for adhering a crown restorative to the tooth, an excess of cement swelling from the surface of adhesion can be favorably removed, the curing time can be suitably adjusted without decreasing the strength of adhesion to the tooth, and a change in the color tone of the cured body can be effectively suppressed.

9 Claims, 1 Drawing Sheet

Fig. 1

DENTAL ADHESIVE

TECHNICAL FIELD

The present invention relates to a dental adhesive such as a dental resin cement having such excellent features that an excess of cement swelling beyond the margin at the time of adhering a crown restorative to the tooth can be favorably removed, the curing time can be suitably adjusted without decreasing the strength of adhesion to the tooth, and the cured body thereof is suppressed from being colored yellow.

BACKGROUND ART

A tooth that has lost its function due to decaying or accident can be restored by, for example, securing, to the tooth, a metallic or ceramic restorative for a crown and an inlay. An adhesive called dental cement is used for securing the crown restorative to the tooth. As the dental cement, there is usually widely used a resin cement and a fluoroaluminosilicate cement (generally called glass ionomer cement).

To adhere the crown restorative to the tooth by using a dental cement, in general, the dental cement is applied in a slightly excess amount to the crown restorative, and the crown restorative is brought into pressed contact with the tooth. Due to the pressed contact, an excess of the dental cement swells beyond the junction portion between the tooth and the crown restorative, which is called marginal portion, and the excess of cement that has swollen is removed. Therefore, the dental cement is offered as a highly fluidizing paste-like composition so that it can be easily applied onto the crown restorative and that an excess amount thereof suitably comes out from the marginal portion. Unless the excess of cement is completely removed, further, the cement that has swollen and cured may not only deteriorate aesthetic appearance but also hurt the tissues in the oral cavity.

Usually, the excess of cement is removed by using an explorer or the like. However, it is difficult to remove the cement by using the explorer if it is in a highly fluidized state without at all being cured. Therefore, the excess of cement is removed in a state where the cement is completely cured or is cured to some extent to lose the fluidity (half-cured state).

Among the dental cements, the resin cement comprises a radically polymerizable monomer and an inorganic or organic filler, and is cured upon being polymerized with a radical polymerization initiator. Upon being blended with an acidic group-containing radically polymerizable monomer, the resin cement firmly adheres to the tooth and to various metals.

The resin cement blended chiefly with an inorganic filler exhibits particularly excellent mechanical strength and durability. When the cement featuring a high mechanical strength is used, the excess of cement can be removed with difficulty after it has been completely cured. Therefore, the excess of cement is removed while it is in a half-cured state. However, the cement is blended with a polymerization initiator in an amount enough for completely curing the cement. Accordingly, the cement stays in a half-cured state for only a short period of time, leaving a difficulty in regard to the timing for removal.

When the resin cement is blended chiefly with an organic filler, on the other hand, the cured body of the cement turns into an elastic material which still can be removed with difficulty by using the explorer after it has been completely cured. Therefore, the excess of cement is removed in a half-cured state. Like when it is blended with an inorganic filler, however, the cement stays in the half-cured state for only a short period of time, leaving a difficulty in regard to the timing for removing the excess of cement.

It becomes very difficult to remove the excess of cement from the portions other than the desired portion once it is completely cured because the resin cement is strongly adhered to the tooth and to the crown restorative irrespective of whether the inorganic filler is contained or the organic filler is contained.

Japanese Unexamined Patent Publication (Kokai) No.9-67222 discloses a technology for delaying the curing time by adding a polymerization inhibitor. In this case, however, the polymerization reaction proceeds at one time after the polymerization inhibitor is all spent out for delaying the polymerization time. Therefore, a fully satisfactory result is not obtained from the standpoint of elongating the timing for removing the excess of cement. There may further arouse such a problem that the strength of adhesion to the tooth decreases with an increase in the amount of the inhibitor.

In order to cure the resin cement, further, there is usually used a system comprising a tertiary amine and an organic peroxide such as benzoyl peroxide as a chemical polymerization initiator. The chemical polymerization initiator comprising this system works to reliably accomplish the curing and establishes safety for the living body. When this system is used, however, there arouses a problem in that the cured body of cement is colored in yellow. The degree of yellow color usually tends to be stronger than the yellow color of natural teeth. After the crown restorative is secured, therefore, the marginal portion of cement becomes so conspicuous as to impair aesthetic appearance.

The above problem of coloring can be solved to some extent by using "a catalyst system of a combination of a pyrimidine trione derivative, a metal compound and an organohalogen compound" disclosed in Japanese Unexamined Patent Publication (Kokai) No. 63-216811. Even when this catalyst system is used, however, there still remains unsolved the problem in that the time margin is not sufficient for removing the excess of cement.

On the other hand, the glass ionomer cement comprises a powder that elutes multiply charged metal ions and an aqueous solution of a polycarboxylic acid, and cures when the powder and the aqueous solution are mixed together as the multiply charged metal ions and the polymer (polycarboxylic acid) undergo the chelate crosslinking. The above cement is easy to handle since it does not usually require the pretreatment for the tooth and offers such a feature that the excess of cement can be favorably removed. Further, the curing mechanism of the glass ionomer cement does not cause a discoloration of the cured body.

Here, however, the reason that the glass ionomer cement permits the excess of cement to be favorably removed is that it is easily collapsed at the time when it is being removed by using the explorer, since the mechanical strength of the completely cure body of cement is smaller than that of the resin cement. Accordingly, while offering the advantage as described above, the glass ionomer cement involves a problem in regard to the durability (reliability) of the cement itself. Another problem of the glass ionomer cement is that when it comes in contact with water such as saliva at the time when it is being curing, the properties such as mechanical strength and the like are deteriorated.

In order to solve the problems possessed by the glass ionomer cement, there has recently been developed and placed in the market a dental cement called resin-reinforced glass ionomer blended with a radically polymerizable monomer and a chemical polymerization initiator in addition to the polycarboxylic acid. In the above cement, the radically polymerizable monomer is polymerized during the curing based on the chelate crosslinking, and the polymer of the radically polymerizable monomer is made present in the cured body that is obtained thereby to improve the mechanical strength that was the defect of the glass ionomer.

Even by using the resin-reinformed glass ionomer, however, the cured body still chiefly comprises the polycarboxylic acid and the chelate (ionomer) of a multiply charged metal-on. Therefore, the mechanical strength is still inferior to that of the resin cement comprising chiefly a polymer of a radically polymerizable monomer, and the reliability is not improved to a sufficient degree.

By using the resin cement having a large strength of adhesion to the tooth and a large mechanical strength, the problem remains with respect to removing the excess of resin and the discoloration of the cured body. By using the glass ionomer cement (containing the resin-reinforced glass ionomer) which permits the excess of cement to be easily removed and exhibiting almost no discoloration), on the other hand, the problem remains with respect to the mechanical strength.

DISCLOSURE OF THE INVENTION

In order to solve the above-mentioned problems, the present inventors have conducted keen study, have discovered the fact that the excess of cement can be favorably removed without almost lowering the strength of adhesion and that the cured body obtained by using a chemical polymerization initiator of the benzoyl peroxide/tertiary amine system can be prevented from developing yellow color when a dental cement containing a radically polymerizable monomer (resin) as a chief curing component is blended with a styrene derivative of a particular structure, and have thus completed the present invention.

According to the present invention, there is provided a dental adhesive comprising:

(A) an acidic group-containing radically polymerizable monomer and (B) a radically polymerizable monomer other than (A) in such amounts as A:B=5:95 to 80:20 based on the mass, and further comprising, per 100 parts by mass of the total amount of said radically polymerizable monomers (A) and (B):

(C) a chemical polymerization initiator in an amount of 0.05 to 15 parts by mass;

(D) a filler in an amount of 20 to 1000 parts by mass; and (E) a compound represented by the following general formula (1), (1)

wherein $R^1$ and $R^2$ are, independently from each other, hydrogen atoms or alkyl groups with 1 to 3 carbon atoms, in an amount of 0.01 to 5 parts by mass.

BEST MODE FOR CARRYING OUT THE INVENTION

The dental adhesive of the present invention is usually used for adhering a crown restorative made of ceramics or a metal to the tooth.

(Radically Polymerizable Monomer Components (A) and (B))

The dental adhesive of the present invention contains, as radically polymerizable components, (A) an acidic group-containing radically polymerizable monomer (hereinafter often called simply acidic monomer) and (B) a radically polymerizable monomer (hereinafter often called non-acidic monomer) other than the above acidic monomer.

Among these radically polymerizable components, (A) the acidic monomer has a property for improving adhesion to the tooth and, further, works to improve adhesion to the crown restorative made of a base metal.

The acidic monomer (A) is a compound having at least one acidic group and at least one radically polymerizable unsaturated group.

Here, the acidic group is such that an aqueous solution or an aqueous suspension of a radically polymerizable monomer having the above group exhibits acidity, and representative examples include those having hydroxyl groups, such as:

a carboxyl group (—COOH),
a sulfo group (—SO$_3$H),
a phosphinico group {=P(=O)OH}, and
a phosphono group {—P(=O)(OH)$_2$}.

In addition to the above hydroxyl group-containing acidic groups, there can be exemplified acid anhydride groups of a structure in which two hydroxyl-containing acid groups are dehydration-condensed, and acid halide groups in which a hydroxyl group in the hydroxyl group-containing acidic group is substituted with halogen.

Further, there is no particular limitation on the radically polymerizable unsaturated group, and any known one may be used. For example, there can be exemplified (meth) acryloyl-type groups such as (meth)acryloyl group, (meth) acryloyloxy group, (meth)acryloylamino group and (meth) acryloylthio group, as well as vinyl group, allyl group and styryl group.

Though not limited thereto only, concrete examples of the above-mentioned acidic monomer (A) are as described below.

(A-1) Radically polymerizable monomers having one carboxyl group in the molecules, such as (meth)acrylic acid, N-(meth)acryloylglycine, N-(meth)acryloylasparagic acid, N-(meth)acryloyl-5-aminosalicilic acid, 2-(meth)acryloyloxyethyl, hydrogen succinate, 2-(meth)acryloyloxyethyl, hydrogen phthalate, 2-(meth)acryloyloxyethyl, hydrogen maleate, 6-(meth)acryloyloxyethylnaphthalene-1,2,6-tricarboxylic acid, O-(meth)acryloyltyrosine, N-(meth)acryloylphenylalanine, N-(meth)acryloyl-p-aminobenzoic acid, N-(meth)acryloyl-o-aminobenzoic acid, p-vinylbenzoic acid, 2-(meth)acryloyloxybenzoic acid, 3-(meth)acryloyloxybenzoic acid, 4-(meth)acryloyloxybenzoic acid, N-(meth)acryloyl-5-aminosalicilic acid, N-(meth)acryloyl- 4-aminosalicilic acid, and acid anhydrides or acid halides of the above radically polymerizable monomers.

(A-2) Radically polymerizable monomers having a plurality of carboxyl groups or acid anhydride groups in the molecules, such as 11-(meth)acryloyloxyundecane-1,1-dicarboxylic acid, 10-(meth)acryloyloxydecane-1,1-dicarboxylic acid, 12-(meth)acryloyloxydodecane-1,1-dicarboxylic acid, 6-(meth)acryloyloxyhexane-1,1-dicarboxylic acid, 2-(meth)acryloyloxyethyl-3'-methacryloyloxy-2'-(3,4-dicarboxybenzoyloxy)propyl succinate, 1,4-bis(2-(meth)acryloyloxyethyl)pyromeritate, N,O-di(meth)acryloyltyrosine, 4-(2-(meth)acryloyloxyethyl)trimeritate anhydride, 4-(2-(meth)acryloyloxyethyl)trimeritate, 4-(meth)acryloyloxyethyl trimeritate, 4-(meth)acryloyloxybutyl trimeritate, 4-(meth)acryloyloxyhexyl trimeritate, 4-(meth)acryloyloxydecyl trimeritate, 4-acryloyloxybutyl trimeritate, 6-(meth)acryloyloxyethylnaphthalene-1,2,6-tricarboxylic acid anhydride, 6-(meth)acryloyloxyethylnaphthalene-2,3,6-tricarboxylic acid anhydride, 4-(meth)acryloyloxyethylcarbonylpropionoyl-1,8-naphthalic acid anhydride, 4-(meth)acryloyloxyethylnaphthalene-1,8-tricarboxylic acid anhydride, 9-(meth)acryloyloxynonane-1,1-dicarboxylic acid, 13-(meth)acryloyloxytridecane-1,1-dicarboxylic acid, 11-(meth)acrylamideundecane-1,1-dicarboxylic acid, and dicarboxylic acids represented by the following formulas, $l + m + n = 3.5$ wherein $R_1$ is a hydrogen atom or a methyl group, as well as acid anhydrides or acid halides having a carboxyl group among the above radically polymerizable monomers.

(A-3) Radically polymerizable monomers (often called radically polymerizable acidic phosphoric acid esters) having a phosphinicoxy group or a phosphonoxy group in the molecules, such as 2-(meth)acryloyloxyethyl dihydrodienephosphate, bis(2-(meth)acryloyloxyethyl)hydrogenphosphate, 2-(meth)acryloyloxyethylphenyl hydrogenphosphate, 10-(meth)acryloyloxydecyl dihydrogenphosphate, 6-(meth)acryloyloxyhexyl dihydrogenphosphate, 2-(meth)acryloyloxyethyl 2-bromoethyl hydrogenphosphate, 2-bromoethyl hydrogenphosphate, 2-(meth)acrylamideethyl dihydrogenphosphate, bis(6-(meth)acryloyloxyhexyl)hydrogenphosphate, bis(10-(meth)acryloyloxydecyl)hydrogenphosphate, and bis{2-(meth)acryloyloxy-(1-hydroxymethyl)ethyl}hydrogenphosphate, as well as acid anhydrides and acid halides of the above radically polymerizable acidic phosphoric acid esters.

(A-4) Radically polymerizable monomers having a phosphono group in the molecules, such as vinylphosphonic acid and p-vinylbenzenephosphonic acid.

(A-5) Radically polymerizable monomers having a sulfo group in the molecules, such as 2-(meth)acrylamide-2-methylpropanesulfonic acid, p-vinylbenzenesulfonic acid and vinylsulfonic acid.

In addition to the radically polymerizable monomers described in (A-1) to (A-5) above, there can be preferably used, as the acidic monomer (A), even those acidic group-containing radically polymerizable monomers that are the components in the dental adhesive compositions as taught in Japanese Unexamined Patent Publication (Kokai) No. 54-11149, Japanese Unexamined Patent Publication (Kokai) No. 58-140046, Japanese Unexamined Patent Publication (Kokai) No. 59-15468, Japanese Unexamined Patent Publication (Kokai) No. 58-173175, Japanese Unexamined Patent Publication (Kokai) No. 61-293951, Japanese Unexamined Patent Publication (Kokai) No. 7-179401, Japanese Unexamined Patent Publication (Kokai) No. 8-208760, Japanese Unexamined Patent Publication (Kokai) No. 8-319209, Japanese Unexamined Patent Publication (Kokai) No. 10-236912, and Japanese Unexamined Patent Publication (Kokai) No. 10-245525.

Among the above acidic monomers (A) in the present invention, it is desired to use the radically polymerizable monomers (A-2) having a plurality of carboxyl groups in the molecules, the radically polymerizable acidic phosphoric acid esters (A-3), and the radically polymerizable monomers having an acid anhydride group in which an acidic group is dehydration-condensed in the above compounds (A-2) and (A-3) from the standpoint of excellent adhesion to the tooth, improved removal of the excess of resin, and preventing discoloration of the cured body. Particularly, it is desired to use the radically polymerizable monomer having an acid anhydride group which is fomed by dehydration-condensing the phosphoric acid (A-3) and the acidic group to the radically polymerizable acid.

Among the above-mentioned radically polymerizable monomers, it is particularly desired to use those represented by the following general formula (2), wherein $R^3$ is a hydrogen atom or a methyl group,

$R^4$ is an organic residue having a valency of 2 to 6 and 1 to 30 carbon atoms, W is an oxygen atom, a sulfur atom or NH, Z is —COOH, —O—P(=O)(OH)$_2$ or —O—P(=O)(OH)(O wherein $R^5$ is an alkyl group having 1 to 10 carbon atoms on the main chain or an aryl group having 6 to 14 carbon atoms constituting a ring, said alkyl group or aryl group may be substituted with a halogen atom, a hydroxyl group, a cyano group, a nitro group, an alkyl group having 1 to 5 carbon atoms, an alkenyl group having 2 to 5 carbon atoms, an alkinyl group having 2 to 5 carbon atoms, an alkoxyl group having 1 to 5 carbon atoms, an acyl group having 2 to 5 carbon atoms or an acyloxy group having 2 to 5 carbon atoms, or may further be substituted with a plurality of the same or different substituents, m and n are, independently from each other, integers of 1 to 5, and m+n is in agreement with the valency of $R^4$.

In the above general formula (2), further, $R^4$ is an organic residue having a valency of 2 to 6 and 1 to 30 carbon atoms. There is, however, no particular limitation except the number of carbons and the valency. For example, the organic residue $R^4$ may contain in the structure thereof bonds other than carbon-to-carbon bond, such as ether bond, ester bond, amide bond, sulfonyl bond, urethane bond or thioether bond or, may further have a substituent such as halogen atom, hydroxyl group, amino group, cyano group or nitro group. Concrete examples of the organic residue include, As the alkyl group $R^5$ having 1 to 10 carbon atoms on the main chain in the group denoted by Z in the general formula (2), there can be preferably exemplified methyl group, ethyl group, n-propyl group, n-butyl group, n-octyl group and n-decyl group and, particularly, the one having 1 to 5 carbon atoms on the main chain is desired. As the substituted alkyl group having the substituent, further, there can be exemplified chloromethyl group, 2-chloroethyl group, 2-bromoethyl group, 2-hydroxyethyl group, 2-hydroxypropyl group, 2,3-dihydroxypropyl group, 6-hydroxyhexyl group, 2-cyanoethyl group, i-propyl group, i-butyl group, t-butyl group, 1-methylpropyl group, 2-ethylhexyl group, 2-propenyl group, cis- or trans-2-butenyl group, 2-propinyl group, methoxymethyl group, 2-methoxyethyl group, 2-ethoxyethyl group, 3-methoxybutyl group, 3-oxabutyl group, 4-oxapentyl group, 3-oxapentyl group, 2-acetyloxyethyl group, 3-acetyloxypropyl group, 2-propionyloxyethyl group, 3-acetyloxy-2-hydroxypropyl group and 2-ethyl-3-hydroxypentyl group.

As the aryl group $R^5$ having 6 to 14 carbon atoms constituting a ring, there can be exemplified phenyl group, 1- or 2-naphthyl group, and 1-, 2- or 9-anthranyl group. As the one in which the alkyl group is substituted with the above substituent, there can be exemplified o-, m- or p-chlorophenyl group, o-, m- or p-bromophenyl group, o-, m- or p-hydroxyphenyl group, 3-hydroxy-2-naphthyl group, o-, m- or p-nitrophenyl group, o-, m- or p-cyanophenyl group, o-, m- or p-methylphenyl group, o-, m- or p-butylphenyl group, 3,4-dimethylphenyl group, 2,4-dimethylphenyl group, o-, m- or p-styryl group, o-, m- or p-(2-propynyl) phenyl group, o-, m- or p-methoxyphenyl group, o-, m- or p-ethoxyphenyl group, 2-, 3- or 4-acetylphenyl group, 2-, 3- or 4-acetyloxyphenyl group, 4-hydroxy-3-methylphenyl group and 4-methyl-2-nitrophenyl group.

In the radically polymerizable monomer represented by the above general formula (2), $R^3$ is particularly preferably a methyl group from the standpoint of removing excess of cement and safety to the living body, $R^4$ is particularly preferably an alkylene group having 1 to 15 carbon atoms, W is particularly preferably an oxygen atom, and Z is particularly preferably $-O-P(=O)(OH)_2$.

As the radically polymerizable acidic phosphoric acid ester (A-3), further, it is particularly desired to use the one represented by the following general formula (3), wherein $R^{3'}$ and $R^{3''}$ are, independently from each other, hydrogen atoms or methyl groups, $R^{4'}$ and $R^{4''}$ are, independently from each other, organic residues having a valency of 2 to 6 and 1 to 30 carbon atoms, W' and W'' are, independently, from each other, oxygen atoms, sulfur atoms or NH, m' and m" are, independently from each other, integers of 1 to 5, (m'+1) is in agreement with a valency of $R^{4'}$, and (m"+1) is in agreement with a valency of $R^{4"}$.

In the above general formula (3), $R^{4'}$ and $R^{4"}$ may be those which are the same as those exemplified concerning $R^4$ in the general formula (2).

Even in the radically polymerizable acidic phosphoric acid ester of the above general formula (3), $R^{3'}$ and $R^{3"}$ are particularly desirably methyl groups, $R^{4'}$ and $R^{4"}$ are particularly desirably alkylene groups with 1 to 15 carbon atoms, and W' and W" are particularly desirably oxygen atoms like those of the general formula (2) from the standpoint of removing excess of cement and safety to the living body.

In the present invention, further, even the acid anhydrides obtained by the dehydration-condensation of the group Z or the group $=P(=O)$—OH in the above general formula (2) and (3) can be preferably used as the acid monomer (A) like the compounds of the general formulas (2) and (3). The acid anhydride may be the one obtained by the dehydration condensation in the molecules of the compound represented by the general formula (2), or may be those obtained by the dehydration condensation among the molecules of the two compounds selected from the group consisting of the compounds represented by the general formulas (2) and (3), vinylsulfonic acid, vinylphosphonic acid and (meth)acrylic acid. The dehydration reaction among the molecules may be the reaction between the same compound (acid) or the reaction between the different compounds (acids). From the standpoint of easy synthesis and availability, it is desired that the acid anhydride is the one obtained by the dehydration condensation in the molecules or is the one obtained by the dehydration condensation between the two molecules of the same acid.

The present invention uses the above acidic monomer (A) as well as the radically polymerizable monomer other than (A), i.e., a non-acidic monomer (B). Use of the non-acidic monomer enhances the mechanical strength of the cured body and improves the reliability of adhesion.

As the non-acidic monomer (B), though there is no particular limitation, there can be preferably used a radically polymerizable monomer of the (meth)acrylic acid ester type from the standpoint of polymerizability and safety to the living body.

Concrete examples of the non-acidic monomer (B) are as described below, which can be used in one kind or in a combination of two or more kinds.

(Monofunctional Radically Polymerizable Monomers)

Methacrylates such as methyl methacrylate, ethyl methacrylate, isopropyl methacrylate, tetrahydrofurfuryl methacrylate, glycidyl methacrylate, 2-hydroxyethyl methacrylate, 2-hydroxypropyl methacrylate, 3-hydroxypropyl methacrylate, 2,3-dihydroxybutyl methacrylate, 2,4-dihydroxybutyl methacrylate, 2-hydroxymethyl-3-hydroxypropyl methacrylate, 2,3,4-trihydroxybutyl methacrylate, 2,2-bis(hydroxymethyl)-3-hydroxypropyl methacrylate, 2,3,4,5-tetrahydroxypentyl methacrylate, diethylene glycol monomethacrylate, triethylene glycol monomethacrylate, tetraethylene glycol monomethacrylate, pentaethylene glycol monomethacrylate, N,N-dimethylaminoethyl methacrylate, as well as acrylates corresponding to these methacrylates.

(Bifunctional Radically Polymerizable Monomers)

(i) Those of the type of aromatic compounds, such as 2,2-bis(methacryloyloxyphenyl)propane, 2,2-bis[4-(3-methacryloyloxy)-2-hydroxypropoxyphenyl]propane, 2,2-bis(4-methacryloyloxyphenyl)propane, 2,2-bis(4-methacryloyloxypolyethoxyphenyl)propane, 2,2-bis(4-methacryloyloxydiethoxyphenyl)propane, 2,2-bis(4-methacryloyloxytetraethoxyphenyl)propane, 2,2-bis(4-methacryloyloxypentaethoxyphenyl)propane, 2,2-bis(4-methacryloyloxydipropoxyphenyl)propane, 2-(4-methacryloyloxydiethoxyphenyl)-2-(4-methacryloyloxydiethoxyphenyl)propane, 2-(4-methacryloyloxydiethoxyphenyl)-2-(4-methacryloyloxyditriethoxyphenyl)propane, 2-(4-methacryloyloxydipropoxyphenyl)-2-(4-methacryloyloxytriethoxyphenyl)propane, 2,2-bis(4-methacryloyloxypropoxyphenyl)propane, 2,2-bis(4-methacryloyloxyisopropoxyphenyl)propane, and acrylates corresponding to these methacrylates;

diadducts obtained by the addition of a diisocyanate compound having an aromatic group, such as diisocyanatemethyl benzene or 4,4'-diphenylmethane diisocyanate and methacrylates having a hydroxyl group, methacrylates having an amino group or acrylates corresponding to these methacrylates (the hydroxyl group-containing methacrylates include 2-hydroxypropyl methacrylate, 3-hydroxypropyl methacrylate, 2-hydroxybutyl methacrylate, 4-hydroxybutyl methacrylate, 5-hydroxypentyl methacrylate, diethylene glycol monomethacrylate, triethylene glycol monomethacrylate, tetraethylene glycol monomethacrylate, pentaethylene glycol monomethacrylate, and the amino group-containing methacrylates include 2-aminoethyl methacrylate, 3-aminopropyl methacrylate, 2-aminopropyl methacrylate, 4-aminobutyl methacrylate, 5-aminopentyl methacrylate and 3-aminopentyl methacrylate).

(ii) Those of the type of aliphatic compounds, such as ethylene glycol dimethacrylate, diethylene glycol dimethacrylate, triethylene glycol dimethacrylate, butylene glycol dimethacrylate, neopentyl glycol dimethacrylate, propylene glycol dimethacrylate, 1,3-butanediol dimethacrylate, 1,4-butanediol dimethacrylate, 1,6-hexanediol dimethacrylate and acrylates corresponding to these methacrylates;

diadducts obtained by the addition of a diisocyanate compound such as hexamethylene diisocyanate, trimethylhexamethylene diisocyanate, diisocyanatemethyl cyclohexane, isophorone diisocyanate, or methylene bis(4-cyclohexylisocyanate) and methacrylates having a hydroxyl group, methacrylates having an amino group, or acrylates corresponding to these methacrylates (the hydroxyl group-containing methacrylates and the amino group-containing methacrylates are as exemplified above).

(Trifunctional Radically Polymerizable Monomers)

Methacrylates such as trimethylolpropane trimethacrylate, trimethylolethane trimethacrylate, pentaerythritol trimethacrylate and trimethylolmethane trimethacrylate, and acrylates corresponding to these methacrylates.

(Tetrafunctional Radically Polymerizable Monomers)

Diadducts obtained by the addition of pentaerythritol tetramethacrylate, pentaerythritol tetraacrylate or diisocyanate compound with glycidol dimethacrylate (the diisocyanate compound includes diisocyanatemethyl benzene, diisocyanatemethyl cyclohexane, isophorone diisocyanate, hexamethylene diisocyanate, trimethylhexamethylene diisocyanate, methylenebis(4-cyclohexylisocyanate), 4,4-diphenylmethanediisocyanate, tolylene-2,4-diisocyanate, etc.).

Among the above-mentioned non-acidic monomers (B) of the present invention, it is desired to use a bifunctional, trifunctional or tetrafunctional radically polymerizable monomer having a plurality of radically polymerizable groups from the standpoint of a large mechanical strength of the cured body that is obtained. By using a monofunctional radically polymerizable monomer in combination, further, the strength of adhesion can be more increased.

In order to improve adhesion to a noble metal that is generally used as a restorative for a crown, it is also allowable to use a radically polymerizable monomer having a sulfur-type functional group as part of the non-acidic monomer (B) as taught in Japanese Unexamined Patent Publication (Kokai) No. 10-1409, Japanese Unexamined Patent Publication (Kokai) No. 10-1473 and Japanese Unexamined Patent Publication (Kokai) No. 8-113763.

In the dental adhesive of the present invention, the above acidic monomer (A) and the non-acidic monomer (B) are used in such amounts as A:B=5:95 to 80:20 and, particularly, 10:90 to 40:60 on the mass basis. When the amount of the acidic monomer (A) is smaller than the above range, the strength of adhesion to the tooth or to the dental metal and, particularly, to the dental enamel, is not sufficient. When the amount of the acidic monomer (A) is larger than the above range, on the other hand, the strength of the cured body decreases and the strength of adhesion to the tooth, too, decreases to some extent.

When the bifunctional, trifunctional or tetrafunctional radically polymerizable monomer (polyfunctional monomer) and the monofunctional monomeric radically polymerizable monomer (monofunctional polymer) are used as the non-acidic monomer (B), it is desired that the polyfunctional monomer is existing in an amount of 10 to 50 parts by mass and the monofunctional polymer is existing in an amount of 40 to 80 parts by mass per 100 parts by mass of the total monomers (sum of the acidic monomer (A) and the non-acidic monomer (B)).

(C) Chemical Polymerization Initiator:

The dental adhesive of the present invention is blended with the chemical polymerization initiator (C). The chemical polymerization initiator comprises a combination of two or more kinds of compounds which, when mixed (contacted) together, form a redox system to generate radicals.

Typical chemical polymerization initiator includes such combinations as organic peroxide/amines, organic peroxide/amines/organosulfinic acids, organic peroxide/amines/aryl borates, aryl borates/acidic compound, and barbituric acid derivative/cupper compound/halogen compound.

Any known organic peroxides can be used for the above chemical polymerization initiator without limitation. Representative examples of the organic peroxide include ketone peroxide, hydroperoxide, diacyl peroxide, dialkyl peroxide, peroxyketal, peroxyester and peroxydicarbonate.

As the ketone peroxide, there can be exemplified methyl ethyl ketone peroxide, methyl isobutyl ketone peroxide, melthyl cyclohexanone peroxide and cyclohexanone peroxide.

As the hydroperoxide, there can be exemplified 2,5-dimethylhexane-2,5-dihydroperoxide, diisopropylbenzene hydroperoxide, cumene hydroperoxide and t-butyl hydroperoxide.

The diacyl peroxide is an organic peroxide which is most desired in the present invention, and its examples include acetyl peroxide, isobutylyl peroxide, benzoyl peroxide, decanoyl peroxide, 3,5,5-trimethylhexanoyl peroxide, 2,4-dichlorobenzoyl peroxide and lauroyl peroxide.

As the dialkyl peroxide, there can be exemplified di-t-butyl peroxide, dicumyl peroxide, t-butylcumyl peroxide, 2,5-dimethyl-2,5-di(t-butylperoxy)hexane, 1,3-bis(t-butylperoxyisopropyl)benzene, and 2,5-dimethyl-2,5-di(t-butylperoxy)hexyne-3.

As the peroxyketal, there can be exemplified 1,1-bis(t-butylperoxy)3,3,5-trimethylcyclohexane, 1,1,-bis(t-butylperoxy)cyclohexane, 2,2-bis(t-butylperoxy)butane, 2,2-bis(t-butylperoxy)octane and 4,4-bis(t-butylperoxy)valeric acid-n-butyl ester.

As the peroxy ester, there can be exemplified α-cumyl peroxyneodecanoate, t-butyl peroxyneodecanoate, t-butyl peroxypivarate, 2,2,4-trimethylpentylperoxy-2-ethyl hexanoate, t-amylperoxy-2-ethyl hexanoate, t-butylperoxy-2-ethyl hexanoate, di-t-butylperoxy isophthalate, di-t-butylperoxy hexahydroterephthalate, t-butylperoxy-3,3,5-trimethyl hexanoate, t-butylperoxy acetate, t-butylperoxy benzoate and t-butylperoxymaleic acid.

As the peroxydicarbonate, there can be exemplified di-3-methoxy peroxydicarbonate, di-2-ethylhexyl peroxydicarbonate, bis(4-t-butylcyclohexyl)peroxy dicarbonate, diisopropyl peroxydicarbonate, di-n-propyl peroxydicarbonate, di-2-ethoxyethyl peroxydicarbonate and diallyl peroxydicarbonate.

As the amines used as the chemical polymerization initiator, though there is no particular limitation, it is desired to use secondary or tertiary amines in which an amino group is bonded to an aryl group or to a pyridyl group, from the standpoint of curing rate. Concretely speaking, there can be used a secondary amine or a tertiary amine represented by the following general formula (4), (4)

wherein $R^6$ is a hydrogen atom or an alkyl group having 1 to 10 carbon atoms on a main chain [the alkyl group may be substituted by a halogen atom, a hydroxyl group, a phenyl group or an alkyl group having 1 to 5 carbon atoms], $R^7$ is an alkyl group having 1 to 10 carbon atoms on a main chain [the alkyl group may be substituted by a halogen atom, a hydroxyl group, a phenyl group or an alkyl group having 1 to 5 carbon atoms], $R^8$ is an aryl group or a pyridyl group having 6 to 14 carbon atoms constituting a ring [the aryl group or the pyridyl group may be substituted with a halogen atom, a hydroxyl group, a cyano group, a nitro group, a carboxyl group, a formyl group, an alkyl group having 1 to 5 carbon atoms, an alkenyl group having 2 to 5 carbon atoms, an alkinyl group having 2 to 5 carbon atoms, an alkoxyl group having 1 to 5 carbon atoms, an acyl group having 2 to 5 carbon atoms, an acyloxy group having 2 to 5 carbon atoms or an alkoxycarbonyl group having 2 to 6 carbon atoms].

As the alkyl group having 1 to 10 carbon atoms on the main chain denoted by $R^6$ and $R^7$, there can be exemplified methyl group, ethyl group, n-propyl group, n-butyl group, n-octyl group, n-decyl group, and as the alkyl group substituted by the above substituent, there can be exemplified chloromelthyl group, 2-chloroethyl group, 2-bromoethyl group, 2-hydroxyethyl group, 2-hydroxypropyl group, 2,3-dihydroxypropyl group, 6-hydroxyhexyl group, i-propyl group, i-butyl group, t-butyl group, 1-methylpropyl group, 2-ethylhexyl group, and benzyl group. Preferred alkyl groups denoted by $R^6$ and $R^7$ have 1 to 5 carbon atoms on the main chain.

As the aryl group having 6 to 14 carbon atoms and constituting a ring denoted by $R^8$, there can be exemplified phenyl group, 1- or 2-naphthyl group or 1-, 2- or 9-anthranyl group and as the aryl group substituted with the above substituent, there can be exemplified o-, m- or p-chlorophenyl group, o-, m- or p-bromophenyl group, o-, m- or p-hydroxyphenyl group, 3-hydroxy-2-naphthyl group, o-, m- or p-nitrophenyl group, o-, m- or p-cyanophenyl group, o-, m- or p-methylphenyl group, o-, m- or p-butylphenyl group, 3,4-dimethylphenyl group, 2,4-dimethylphenyl group, o-, m- or p-styryl group, o-, m- or p-(2-propynyl) phenyl group, o-, m- or p-methoxyphenyl group, o-, m- or p-ethoxyphenyl group, 2-, 3- or 4-acetylphenyl group, 2-, 3- or 4-acetyloxyphenyl group, 4-hydroxy-3-methylphenyl group, and 4-methyl-2-nitrophenyl group. A preferred aryl group denoted by $R^8$ has 6 to 10 carbon atoms to constitute a ring.

Among the amine compounds represented by the above general formula (4), the secondary amines that can be preferably used are N-methylaniline, N-(2-hydroxyethyl) aniline, and N-methyl-p-toluidine. As the tertiary amine that can be preferably used, there can be exemplified N,N-dimethylaniline, N,N-diethylaniline, N,N-di-n-butylaniline, N,N-dibenzylaniline, N-methyl-N-(2-hydroxyethyl)aniline, N,N-di(2-hydroxyethyl)aniline, p-bromo-N,N-dimethylaniline, p-chloro-N,N-dimethylaniline, N,N-dimethyl-p-toluidine, N,N-diethyl-p-toluidine, p-tolyldiethanolamine, N-methyl-N-(2-hydroxyethyl)-p-toluidine, p-dimethylaminobenzaldehyde, p-dimethylaminoacetophenone, p-dimethylaminobenzoic acid, p-dimethylaminobenzoic acid ethyl ester, p-dimethylaminobenzoic acid amyl ester, N,N-dimethylanthranilic acid methyl ester, p-dimethylaminophenetyl alcohol, N,N-dimethyl-3,5-xylidene, 4-dimethylaminopyridine, N,N-dimethyl-α-naphthylamine and N,N-dimethyl-β-naphthylamine.

As the organosulfinic acid compound used as one component in the chemical polymerization initiator, though not necessarily limited thereto only, there can be exemplified lithium salts, sodium salts, potassium salts, magnesium salts, ammonium salts, pyridinium salts and quinolinium salts of sulfinic acids, such as benzene sulfinic acid, o-toluenesulfinic acid, m-toluenesulfinic acid, p-toluenesulfinic acid, 2,3-dimethylbenzenesulfinic acid, 3,5-dimethylbenzenesulfinic acid, and α-naphthalenesulfinic acid.

The aryl borate compound used as one component of the chemical polymerization initiator is the one having 1 to 4 boron-aryl bonds in a molecule and, preferably, the one having 3 to 4 boron-aryl bonds in a molecule.

Concretely speaking, the aryl borate compound is a salt of borate having 3 or 4 boron-aryl bonds in a molecule. Examples include metal salts such as sodium salt, lithium salt, potassium salt and magnesium salt; ammonium salts such as tetrabutylammonium salt, tetramethylammonium salt, tetraethylammonium salt, tributylammonium salt and triethanolammonium salt; piridinium salts such as methylpiridinium salt, ethylpiridinium salt and butylpiridinium salt; and quinolinium salts such as methylquinolinium salt, ethylquinolinium salt and butylquinolinium salt. Here, examples of the borate compound having three boron-aryl bonds in a molecule include monoalkyltriphenylboron, monoalkyltris(p-chlorophenyl)boron, monoalkyltris(p-fluorophenyl)boron, monoalkyltris(3,5-bistrifluoromethyl)phenylboron, monoalkyltris[3,5-bis(1,1,1,3,3,3-hexafluoro-2-methoxy-2-propyl)phenyl]boron, monoalkyltris(p-nitrophenyl)boron, monoalkyltris(m-nitrophenyl)boron, monoalkyltris(p-butylphenyl)boron, monoalkyltris(m-butylphenyl)boron, monoalkyltirs(p-butyloxyphenyl)boron, monoalkyltris(m-butyloxyphenyl)boron, monoalkyltirs(p-octyloxyphenyl)boron, and monoalkyltirs(m-octyloxyphenyl)boron. Further, examples of the borate having four boron-aryl bonds in a molecule include tetraphenylboron, tetrakis(p-chlorophenyl)boron, tetrakis(p-fluorophenyl)boron, tetrakis(3,5-bistrifluoromethyl)phenylboron, tetrakis[3,5-bis(1,1,1,3,3,3-hexafluoro-2-methoxy-2-propyl)phenyl] boron, tetrakis(p-nitrophenyl)boron, tetrakis(m-nitrophenyl) boron, tetrakis(p-butylphenyl)boron, tetrakis(m-butylphenyl)boron, tetrakis(p-butyloxyphenyl)boron, tetrakis(m-butyloxyphenyl)boron, tetrakis(p-octyloxyphenyl)boron, and tetrakis(m-octyloxyphenyl)boron. In the above borates, alkyl is any one of n-butyl, n-octyl or n-dodecyl.

As the barbituric acid derivative used as one component of the chemical polymerization initiator, there can be exemplified, for example, 5-butyl(thio)barbituric acid, 1,3,5-trimethyl(thio)barbituric acid, 1-benzyl-5-phenyl(thio)barbituric acid, 1-cyclohexyl-5-methyl(thio)barbituric acid and 1-cyclohexyl-5-butyl(thio)barbituric acid.

Concrete examples of the copper compound include copper acetylacetonate, cupric acetate, copper oleate, cupric chloride and cupric bromide.

As the halogen compound, there can be preferably used dilauryldimethylammonium chloride, lauryldimethylbenzylammonium chloride, benzyltrimethylammonium chloride, tetramethylammonium chloride, benzyldimethylcetylammonium chloride, and dilauryldimethylammonium bromide.

In the chemical polymerization initiator using the above various compounds in combination, it is desired that the combination of organic peroxide/amines uses amines in an amount of 0.01 to 4 mols and, particularly, 0.05 to 3 mols per mol of the organic peroxide.

In the combination of organic peroxide/amines/organosulfinic acids, it is desired that the amines are used in an amount of 0.01 to 4 mols and, particularly, 0.05 to 3 mols, and the organic sulfinic acid is used in an amount of 0.01 to 3 mols and, particularly, 0.05 to 2 mols per mol of the organic peroxide.

In the combination of organic peroxide/amins/aryl borates, it is desired that the amines are used in an amount of 0.01 to 4 mols and, particularly, 0.05 to 3 mols, and aryl borates are used in an amount of 0.01 to 3 mols and, particularly, 0.05 to 2 mols per mol of the organic peroxide.

In the combination of aryl borates/acidic compound, the above-mentioned acidic group-containing radically polymerizable monomer (acidic monomer (A)) corresponds to the acidic compound. Therefore, the acidic compounds needs not be particularly used as the chemical polymerization initiator. As required, however, there can be used, as an acidic compound, an inorganic acid such as hydrochloric acid, nitric acid, sulfuric acid or phosphoric acid, or an organic acid such as acetic acid, maleic acid, citric acid, malonic acid, oxalic acid, propanesulfonic acid, benzenesulfonic acid, or toluenesulfonic acid. In this case, the acidic compound is used as required in an amount of not larger than 1 mol per mol of the aryl borates.

In the combination of barbituric acid derivative/copper compound/halogen compound, it is desired that the copper compound is used in an amount of 0.000001 to 0.01 mol and, particularly, 0.00001 to 0.002 mols and that the halogen compound is used in an amount of 0.0001 to 1 mol and, particularly, 0.001 to 0.2 mols per mol of the barbituric acid derivative.

The chemical polymerization initiators of the above combinations can be used alone or in a combination of two or more kinds.

In the present invention, it is desired to use a chemical polymerization initiator of organic peroxide/amines from a standpoint of obtaining a large strength of adhesion to the tooth or easy handling. In the chemical polymerization initiator of organic peroxide/amines, in particular, the amine is partly neutralized with the acidic monomer (A). As a result, the curing rate is suitably delayed offering an advantage of facilitating the operation for removing excess of cement. When the chemical polymerization initiator of this type is used, further, a problem arouses in regard to discoloration (yellowing) of the cured product as described already. In the present invention, however, use of the styrene derivative (E) helps effectively avoid the problem of discoloration as will be described later, which is a great advantage of the present invention.

In the present invention, the chemical polymerization initiator is blended in an amount of 0.05 to 15 parts by mass and, particularly, 0.5 to 8 parts by mass per 100 parts by mass of the whole monomers (sum of the acidic monomer (A) and the non-acidic monomer (B)). When used in an amount greater than the above range, the curing rate becomes so fast that it becomes difficult to remove the excess of cement. Further, the cured body is often discolored. When the chemical polymerization initiator is blended in an amount smaller than the above range, the curing rate becomes too slow, and the cured body exhibits poor properties, i.e., unsatisfactory mechanical strength.

The chemical polymerization initiator comprises a combination of two or more kinds of compounds, and the amount of the chemical polymerization initiator that is blended is the total amount of the compounds. In the combination of aryl borates/acidic compound, the acidic monomer (A) works as an acidic compound. Therefore, the amount of the aryl borates is regarded to be the amount of the chemical polymerization initiator.

In the present invention, the chemical polymerization initiator can be used by being coated with a high molecular compound in order to improve the preservation stability of the chemical polymerization initiator. As the high molecular compound used for the coating, there can be exemplified ethyl cellulose, polyethyl methacrylate and polyethylene glycol. There is no particular limitation on the coating method, and any known coating method can be employed. Preferably, the coating method can be carried out by using, for example, a rolling/fluidizing granulating coating device which has been placed in the market in the name of MP-10, manufactured by Powreck Co.

(D) Fillers:

The dental adhesive of the present invention is blended with a filler (D) in an amount of 20 to 1000 parts by mass and, particularly, 70 to 400 parts by mass per 100 parts by mass of the whole monomers (sum of the monomers (A) and (B)). When the amount of the filler that is blended is smaller than the above range, the viscosity of the adhesive in a paste-like state becomes so low (fluidity becomes so high) that it becomes difficult to adhere the crown restorative to the tooth by using the adhesive. Further, it becomes difficult to remove excess of cement and, besides, the cured body that is obtained exhibits decreased mechanical strength. When the amount of the filler that is blended becomes greater than the above range, on the other hand, the adhesive exhibits too increased viscosity to make it difficult to carry out the adhesion operation. Depending upon the cases, furthermore, it becomes difficult to prepare the paste of the adhesive itself.

Generally, the fillers can roughly be separated into organic fillers and inorganic fillers.

Organic fillers may be methyl polymethacrylate, ethyl polymethacrylate, methyl melthacrylate/ethyl methacrylate copolymer, crosslinked methyl polymethacrylate, crosslinked ethyl polymethacrylate, ethylene/vinyl acetate copolymer, styrene/butadiene copolymer, acrylonitrile/styrene copolymer, and acrylonitrile/styrene/butadiene copolymer, which can be used alone or as a mixture of two or more kinds.

Inorganic fillers may be quartz, silica, alumina, silica-titania, silica-zirconia, lanthanum glass, barium glass, strontium glass, and fluoroalumino silicate glass. They may be used alone or being mixed in two or more kinds.

In the present invention, it is desired to use an inorganic filler. Among the inorganic fillers, it is more desired to use a fluoroaluminosilicate glass to impart such a property that fluorine is gradually released.

There is no particular limitation on the fluoroalumino silicate glass provided it serves as a filler of acid fluoride glass of aluminum and silicon. There can be used those that are generally used as a acid reactive filler or an ion-eluting filler in the dental adhesives. In the present invention, there is preferably used the one containing, by ionic mass %, 10 to 33 mass % of silicon, 4 to 30 mass % of aluminum, 5 to 36 mass % of alkaline earth metal, 0 to 10 mass % of alkali metal, 0.2 to 16 mass % of phosphor; 2 to 40 mass % of fluorine, and the remainder of oxygen. As the alkaline earth metals, there can be used calcium, magnesium, strontium and barium. As the alkali metals, further, there can be used sodium, lithium and potassium. Among them, sodium is particularly preferred. As required, further, aluminum may be partly substituted by titanium, yttrium, zirconium, hafnium, tantalum or lanthanum.

The fluoroaluminosilicate glass can be produced by, for example, mixing metal compounds such as silica, alumina, fluorite, cryolite and aluminum fluoride together, sintering them at 1100 to 1300° C. followed by milling, or by the sol-gel method.

In the present invention, the inorganic filler can be used with its surfaces being treated by a known method by using a surface treating agent such as silane coupling agent or the like. As the silane coupling agent, there can be preferably used methyltrimethoxysilane, methyltriethoxysilane, methyltrichlorosilane, dimethyldichlorosilane, trimethylchlorosilane, vinyltrichlorosilane, vinylethoxysilane, γ-methacryloyloxypropyltrimethoxysilane, γ-chloropropyltrimethoxysilane and hexamethyldisilazane.

When a fluoroaluminosilicate glass is used as the inorganic filler, the fluoroaluminosilicate glass may be coated with a high molecular compound in order to improve kneading property between the powder and the solution.

There is no particular limitation on the shape of the filler that can be used in the present invention; i.e., the filler may assume amorphous particulate shape obtained through an ordinary milling or may assume a spherical particulate shape.

Though there is no particular limitation on the particle diameter of the filler, as the particle diameter increases, the paste of adhesive exhibits a decreased viscosity despite of the same amount of the filler, and exhibits excellent fluidity when the crown restorative is press-contacted to the tooth. As the particle diameter decreases, on the other hand, the film thickness decreases after it is press-adhered making it possible to restore the tooth in a state where the crown restorative is intimately adhered to the tooth. By taking them into consideration, according to the present invention, it is desired that the filler has an average particle diameter of 0.01 to 100 μm and, particularly, 0.1 to 50 μm.

(E) Styrene Derivatives:

The dental adhesive of the present invention is blended with a compound (styrene derivative) represented by the following general formula (1), (1)

wherein $R^1$ and $R^2$ are, independently from each other, hydrogen atoms or alkyl groups having 1 to In the above general formula (1), the alkyl group having 1 to 3 carbon atoms is a methyl group, an ethyl group, an n-propyl group or an i-propyl group.

There is no particular limitation on the styrene derivative that is used in the present invention as far as it is represented by the above general formula (1). From the standpoint of easy availability, however, it is desired that the styrene derivative is a 2,4-diphenyl-4-methyl-1-pentene in which $R^1$ and $R^2$ are both methyl groups. As required, further, it is allowable to use in combination a plurality of styrene derivatives in which $R^1$ and $R^2$ are different from each other.

According to the present invention, the excess of resin can be favorably removed being blended with the above styrene derivative without almost lowering the strength of adhesion. With the dental adhesive of the present invention blended with the above styrene derivative, it is allowed to extend the time from when it starts curing to lose the fluidity until when it is ends of curing. Therefore, an operation time margin for removing excess of resin becomes longer than that of the conventional dental adhesives. Besides, the cured body that is obtained exhibits excellent properties such as mechanical strength and strength of adhesion to the tooth and to the crown restorative.

Figure 1:
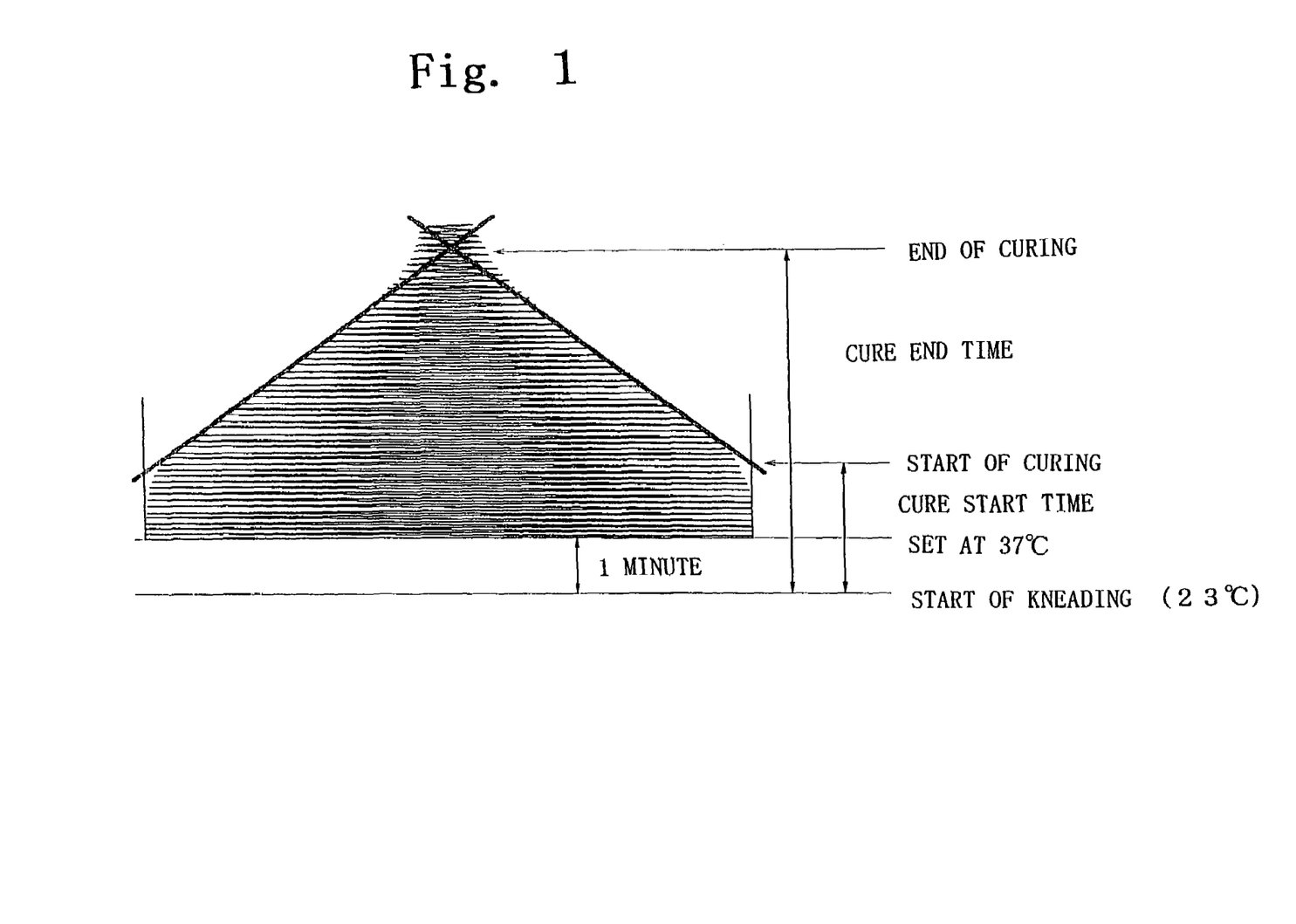
FIG. 1 is a diagram illustrating how to calculate the cure start time and the cure end time from the measured results by using a dental rheometer.

Reference should be made to FIG. 1 which illustrates the effect for removing the excess of resin (cement). That is, a dental rheometer, type B (manufacutred by Seiki Co.), is left to stand at 37° C. constant for one hour, the distance between the sample plates is adjusted to be 0.15 mm, 0.2 g of a paste of the dental adhesive is set to the sample plates one minute after the start of the kneading, and a change in the fluidity of the adhesive is measured after it is set. In FIG. 1, the ordinate represents the passage of time and the abscissa represents the fluidity of the paste (the fluidity decreases with a decrease in the width). The dental rheometer is turned clockwise and counterclockwise at regular intervals with a predetermined torque to measure the rotational distance (rotational angle) at that moment.

That is, when a component containing the chemical polymerization initiator and a component containing the monomer component are kneaded together, the fluidity remains very high for a while after the start of the kneading, and the rheometer turns nearly completely. During this period, the fluidity is too high, and the paste can be removed with difficulty by using explorer. After a while from the kneading, the polymerization proceeds and the fluidity starts decreasing (start of curing), and the rotational distance gradually decreases with the application of the same torque. Then, finally, the fluidity so decreases that the rheometer does not almost turn (end of curing).

After the curing, the excess of resin exhibits an increased mechanical strength and, besides, strongly adheres even onto the tooth and the crown restorative, and it becomes very difficult to remove the excess of resin.

Removal of the excess of resin is affected by the adhering property and the mechanical property of the cured body that is finally obtained. In general, however, the operation time margin for the removal increases with an increase in the time from the start of curing until the end of curing as measured by using the dental rheometer, which means that the dental adhesive can be excellently removed.

As will be demonstrated later by way of Examples, the dental adhesive of the present invention makes it possible to adjust the time from the start of curing until the end of curing to be from 1.0 to 5.0 minutes as measured by using the dental rheometer, and undergoes the curing over a period of time sufficient for removing the excess resin without giving burden to a patient. The strength of adhesion of the cured body to the tooth can be adjusted to be 6 to 10 MPa, the strength of adhesion to the enamel can be adjusted to be 8 to 15 MPa, and the compression strength can be adjusted to be 140 to 230 MPa. Thus, favorable adhesiveness and mechanical strength are obtained.

When a widely known polymerization inhibitor or a polymerization adjusting agent is blended, the time for starting the curing is simply delayed or the strength of adhesion and mechanical strength are deteriorated. The fact that the operation time margin only can be extended without affecting various properties is a distinguished advantage of the adhesive of the present invention stemming from the styrene derivative represented by the above general formula (1).

As will be understood from Examples appearing later, the dental adhesive of the present invention blended with the styrene derivative effectively prevents the yellowing of the cured body of when there is used a chemical polymerization initiator such as organic peroxide/amines.

In the present invention, the styrene derivative represented by the above general formula (1) is blended in an amount in a range of from 0.01 to 5 parts by mass, preferably, from 0.1 to 2 parts by mass and, most preferably, from 0.5 to 2 parts by mass per 100 parts by mass of the whole monomers (sum of the monomer (A) and the monomer (B)). Being blended in such an amount, it is allowed to extend the time (operation time margin) from the start of curing until the end of curing without affecting the mechanical strength or the adhering strength of the finally obtained curing body. When the blending amount is too small, the operation margin time is not extended to a sufficient degree or the yellowing is not suppressed to a sufficient degree. When the blending amount is too large, on the other hand, the operation time margin becomes long and the restoration (therapy) is not completed until the curing ends. Further, the blending in very too large amounts affects the mechanical strength and the adhering strength of the finally obtained cured body.

(Other Blending Agents)

The dental adhesive of the present invention can be blended with known additives within ranges of not deteriorating the properties. Such additives may include polymerization inhibitor, antioxidant, pigment, dye, ultraviolet-ray absorber, water, organic solvent, viscosity-increasing agent, and the like.

(How to Use)

There is no particular limitation on the method of using the dental adhesive of the present invention. The dental adhesive of the invention, however, can be preferably used according to, for example, a method described below.

A paste obtained by mixing the dental adhesive of the invention is applied to a variety of dental crown restoratives, press-adhered to the tooth before it starts curing, whereby the adhesive polymerizes and cures to adhere the restorative to the tooth.

In order to further improve the adhesiveness, the tooth surfaces may have been treated in advance with a tooth surface-treating agent. When the crown restorative is a noble metal or ceramics, the surfaces may preferably be treated with a dental surface-treating agent called noble metal primer or ceramics primer. Known surface-treating agents can be used without any limitation.

Though there is no particular limitation on the manner of packaging, the dental adhesive of the present invention can be favorably used being packaged in a manner, for example, as described below.

That is, a powdery component is prepared by using a filler (D) and at least one component of the chemical polymerization initiator (C), and a liquid component is prepared by using an acidic monomer (A), a non-acidic monomer (B), a styrene derivative (E) and the remaining components in the chemical polymerization initiator (C). At the time of use, the powdery component and the liquid component are mixed at a predetermined ratio to prepare a dental adhesive of the present invention. Here, when the chemical polymerization initiator (E) contains the components that undergo the decomposition due to such acids as aryl borates or sulfinates, or contains the components such as organic peroxides that are decomposed by heating and exhibit radical polymerization initiating ability by themselves, it is desired that such components are blended in the powdery component.

The packaging state other than the one described above may be employed as required, as a matter of course.

EXAMPLES

The present invention will now be concretely described by way of Examples to which only, however, the invention is in no way limited.

1. Described below are Abbreviations of the Compounds used in Examples.
(A) Acidic group-containing radically polymerizable monomers (acidic monomers).
   PM: 2-methacryloyloxyethyl dihydrogen phosphate
   PM2: bis(2-methacryloyloxyethyl)hydrogen phosphate
   MAC-10: 11-methacryloyloxy-1,1-undecanedicarboxylic acid
(B) Radically polymerizable monomers (non-acidic monomers) other than (A).
   HEMA: 2-hydroxyethyl methacrylate
   UDMA: 1,6-bis(methacrylethyloxycarbonylamino)-2,2,4-trimethyl hexane
   MMA: methyl methacrylate
   3G: triethylene glycol dimethacrylate
(C) Chemical polymerization initiators.
   BPO: benzoyl peroxide
   PBTEOA: triethanol ammonium salt of tetraphenylboron
   PTSNa: sodium p-toluenesulfinate
   DEPT: N,N-bis(2-hydroxyethyl)amino-p-toluidine
   DMPT: N,N-dimethylamino-p-toluidine
(D) Fillers.
   FASG: fluoroaluminosilicate glass filler {Tokuso Glass Ionomer Cement Powder (manufactured by Tokuyama Co.)}
   SE-1: Spherical silica having an average particle diameter of 1 μm (Excelica SE-1, manufactured by Tokuyama Co.)
   Si—Zr: Spherical silica-zirconia filler having an average particle diameter of 10 μm
   Si—Ti: Amorphous silica-titania filler having an average particle diameter of 15 μm
   PMMA: polymethyl methacrylate having an average particle diameter of 20 μm and a molecular weight of 300,000
(E) Compounds represented by the general formula (1).
   Me—Me: 2,4-diphenyl-4-methyl-1-pentene
   Me—Et: 2,4-diphenyl-4-methyl-1-hexene
   Et—Et: 2,4-diphenyl-4-ethyl-1-hexene 2. Described Below are the Methods of Evaluating the Properties in Examples and in Comparative Examples.

(Measurement of Adhering Strength)

A bovine foretooth was pulled out within 24 hours after the slaughter, and the enamel surface or the tooth surface was ground with a #800 emery paper while pouring water so as to become in parallel with the lip surface. Next, the compressed air was blown onto the surface for about 10 seconds to dry it, a double-sided tape having a hole of a diameter of 3 mm perforated therein was secured to the surface, the adhesive adjusted just before the use was applied into the hole, and a stainless steel attachment was press-adhered thereon.

The above adhesion test piece was left to stand at 37° C. at a humidity of 100% for one hour, immersed in water maintained at 37° C. for 24 hours, and was pulled by using a pulling tester (autograph, manufactured by Shimazu Mfg. Co.) at a crosshead speed of 2 mm/min to measure the tensile adhering strength (also simply referred to as "adhering strength") to the tooth.

Eight test pieces prepared under the same conditions were measured for their tensile adhering strength, and an average value of the tensile adhering strengths was regarded to be the adhering strength of the adhesive composition.

(Measurement of the Curing Time)

A dental rheometer, type B (manufactured by Seiki Co.), was left to stand at 37° C. constant for one hour, and the distance between the sample plates was adjusted to be 0.15 mm.

0.2 Grams of the sample dental adhesive was kneaded, and was set onto the sample plates one minute after the start of kneading. After set to the sample plates, a change in the fluidity of the adhesive was measured to calculate a time (cure start time) at which the fluidity starts changing and a time (cure end time) at which the fluidity ends changing.

The same sample was measured twice, and the cure start time and the cure end time were calculated from the average values.

(Evaluation of Removal of Excess of Cement)

A bovine foretooth was pulled out within 24 hours after the slaughter, and the enamel was ground with a #800 emery paper while pouring water so as to become in parallel with the lip surface. Next, the compressed air was blown onto the surface for about 10 seconds to dry it, and the bovine foretooth was left to stand at 37° C. at a humidity of 100% for one hour. 0.2 Grams of the adhesive was kneaded, applied onto the enamel, an aluminum plate measuring 5 mm×5 mm was placed thereon and after 2 minutes have passed from the start of kneading, the sample was preserved at 37° C. and a humidity of 100%. Then, after 30 seconds have passed, the removal of excess of resin on the sample by using an explorer was evaluated. The time at which it was made possible for the first time to easily remove the excess of resin was subtracted from the time in which the curing has so proceeded that the excess of resin could not be removed with the explorer, and the thus obtained time was evaluated to be the removal possible time.

(Color Tone)

A sample adhesive was poured into a perforated polyacetal mold having a diameter of 7 mm and a height of 3 mm, press-contacted with a polypropylene film, left to stand in a constant-temperature chamber maintained at 37° C. and a humidity of 100% for one hour, and was immersed in water maintained at 37° C. for 24 hours to obtain a cured body.

The color tone of the cured body was measured by using a color-difference meter (TC-1800MK White-Back, manufactured by Tokyo Denshoku Co.) in compliance with JIS Z 8729. The testing was conducted by using two test pieces at a total of upper and lower four points, and was evaluated in terms of an average of b* representing a yellow color tone of the cured body. The degree of yellow color decreases with a decrease in b*.

(Strength of a Cured Body)

An adhesive composition was poured into a perforated polyacetal mold having a diameter of 4 mm and a height of 3 mm, press-contacted with a polypropylene film, left to stand in a constant-temperature chamber maintained at 37° C. and a humidity of 100% for one hour, and was immersed in water maintained at 37° C. for 24 hours to obtain a cured body.

The cured body was compressed by using a compression tester (autograph, manufactured by Shimazu Mfg. Co.) at a crosshead speed of 10 mm/min to measure the compression strength of the cured body.

Four test pieces manufactured under the same conditions were measured for their compression strengths, and an average value thereof was regarded to be a value of the strength of the cured body.

Example 1

7 Parts by mass of PM, 13 parts by mass of PM2, 50 parts by mass of HEMA, 30 parts by mass of UDMA, 0.3 parts by mass of DEPT and 1 part by mass of Me—Me were mixed together to obtain liquid components in the form of a homogeneous solution.

Separately, 160 parts by mass of FASG, 70 parts by mass of SE-1, 3.5 parts by mass of BPO and 0.7 parts by mass of PBTEOA were mixed together to obtain powdery components in the form of a homogeneous powder.

The liquid components and the powder components were kneaded together at the above mass ratios until the mixture became homogeneous in order to evaluate the strength of adhesion to the tooth, curing time, removal possible time, b* of the cured body, and the compression strength of the cured body.

As a result, a large strength of adhesion to the tooth was obtained; i.e., strength of adhesion to the tooth of 7.6 MPa and strength of adhesion to the enamel of 10.2 MPa. The cure start time was 3.8 minutes, the cure end time was 6.3 minutes, and the time of half-cured state was 2.5 minutes.

The time in which the excess of cement could be virtually removed was 180 seconds. Further, b* representing the degree of yellow color of the cured body was 10.1, and the coloring was small. The compression strength of the cured body was 210 MPa. The results were as shown in Table 2.

Examples 2 to 20

Physical properties were evaluated in the same manner as in Example 1 but changing the adhesive compositions as shown in Table 1. The evaluated results were as shown in Table 2.

Comparative Example 1

A curable composition was prepared in the same manner as in Example 1 but using 0.1 part by mass of a 2,6-di-t-butyl-4-methylphenol (BHT) which is a polymerization inhibitor in place of 1 part by mass of a styrene derivative (Me—Me) which is the component E used in Example 1, and the properties were evaluated.

As a result, there was obtained a strength of adhesion to the tooth lower than that of Example 1; i.e., strength of adhesion to the tooth was 3.1 MPa and the strength of adhesion to the enamel was 5.0 MPa. The cure start time was 4.7 minutes, the cure end time was 5.3 minutes, and the time of half-cured state was 0.6 minutes. The time in which the excess of cement could be virtually removed was 50 seconds, which was shorter than that of Example 1. Further, b* representing the degree of yellow color of the cured body was 12.8, and the coloring was large. The compression strength of the cured body was 197 MPa. The results were as shown in Table 2.

Comparative Example 2

A curable composition was prepared in the same manner as in Example 3 but using 0.005 parts by mass of a hydroquinone (HQ) which is a polymerization inhibitor in place of 0.8 parts by mass of a styrene derivative (Me—Me) which is the component E, and the properties were evaluated.

As a result, there was obtained a strength of adhesion to the tooth lower than that of Example 3; i.e., strength of adhesion to the tooth was 2.7 MPa and the strength of adhesion to the enamel was 4.4 MPa. The cure start time was 5.8 minutes, the cure end time was 6.6 minutes, and the time of half-cured state was 0.8 minutes. The time in which the excess of cement could be virtually removed was 60 seconds, which was shorter than that of Example 3. Further, b* representing the degree of yellow color of the cured body was 14.3, and the coloring was large. The compression strength of the cured body was 201 MPa. The results were as shown in Table 2. There was observed a delay of the curing time due to the use of the polymerization inhibitor. However, there was observed no extension in the time in which the excess of cement could be removed. There was further observed a decrease in the strength of adhesion to the tooth.

Comparative Examples 3 to 10

Physical properties were evaluated in the same manner as in Example 1 but changing the adhesive compositions as shown in Table 1. The results of evaluation were as shown in Table 2.

Comparative Examples 3 to 5 were those of the cases of when the acidic monomer which is the component (A) was lacking in Examples 1, 3 and 4. The strengths of adhesion to the tooth were considerably small; i.e., strengths of adhesion to the tooth were 2.1 MPa, 1.6 MPa and 2.8 MPa, and the strengths of adhesion to the enamel were 4.1 MPa, 3.8 MPa and 4.9 MPa. Further, the times of the half-cured state were 1.1 minutes, 1.4 minutes and 1.5 minutes and, hence, the removal possible times were 100 seconds, 120 seconds and 120 seconds, which were shorter than the times in Examples 1, 3 and 4. Moreover, the values b* were 12.9, 13.9 and 12.1, and the degrees of coloring were greater than those of Examples 1, 3 and 4.

From the foregoing, it is learned that the acidic monomer (A) in the dental adhesive of the present invention not only helps improve the adhesiveness to the tooth but also helps extend the removal possible time and lowers the degree of coloring.

Comparative Examples 6 and 8 were concerned to the adhesives of when the styrene derivative which is the component (E) was not blended.

The strengths of adhesion to the tooth were the same as those of Examples. However, the times of the half-cured state (cure end time—cure start time) were all not longer than 0.6 minutes. Even from the standpoint of practically removing the cement, the removal possible time was shorter than 30 seconds. The values b* representing the degrees of coloring were 13.1 and 13.5 exhibiting obviously yellowish color as compared to Examples 1 and 3.

Comparative Examples 7 and 9 were concerned to the adhesives of when the styrene derivative which is the component (E) was blended in an amount of 10 parts by mass greatly exceeding the range of blending of the invention.

The strengths of adhesion to the tooth were apparently lower than those of Examples, the compression strengths of the cured bodies were about 90 MPa, and the cements could not be used for the dental application to a satisfactory degree.

Comparative Example 10 was concerned to the adhesive without blended with the non-acidic monomer (B) which is the essential component of the present invention, and the compression strength of the cured body was as low as 120 MPa. Besides, the strengths of adhesion to the tooth and to the enamel were slightly smaller.

Comparative Example 11

A dental adhesive of a composition shown in Table 1 was prepared. Without blended with the chemical polymerization initiator of the component (C), however, the adhesive did not cure. Accordingly, the strength of adhesion was 0.

Comparative Example 12

A dental adhesive of a composition shown in Table 1 was prepared. However, since the amount of filler which is the component (D) was so small, the viscosity of the obtained adhesive paste was very low. When an evaluation sample to be removed was prepared, therefore, the compound flew and spread widely and thinly, and could not be removed with the explorer.

Comparative Example 13

It was attempted to prepare a dental adhesive of a composition shown in Table 1. However, the amount of the filler was so large that a paste-like homogeneous composition could not be obtained.

TABLE 1

| | Liquid component | | | | | | | | | | | |
|---|---|---|---|---|---|---|---|---|---|---|---|---|
| | Component A | | | Component B | | | | Component C | | Component E | | |
| | PM | PM2 | MAC-10 | HEMA | MMA | UDMA | 3G | DEPT | DMPT | Me—Me | Me—Et | Et—Et |
| Ex. 1 | 7 | 13 | | 50 | | 30 | | 0.3 | | 1 | | |
| Ex. 2 | 7 | 13 | | 50 | | 30 | | 0.3 | | 5 | | |
| Ex. 3 | 7 | 13 | | 50 | | 30 | | 1.6 | | 0.8 | | |
| Ex. 4 | | | 20 | 10 | 70 | | | 2 | | 0.8 | | |
| Ex. 5 | 2 | 8 | 10 | 30 | 20 | 30 | | 3 | | 2 | | |
| Ex. 6 | 1 | 4 | 5 | 50 | 10 | | 30 | 2 | | 3 | | |
| Ex. 7 | 7 | 13 | 20 | 30 | | 30 | | 0.4 | | 0.01 | | |
| Ex. 8 | | 20 | | 50 | | | 30 | | 0.9 | 0.2 | | |
| Ex. 9 | 7 | 13 | 10 | 40 | | 30 | | 1.5 | | | | 1 |
| Ex. 10 | 4 | 16 | | 50 | | | 30 | | 1.6 | | 0.8 | |
| Ex. 11 | 7 | 13 | | 60 | | 20 | | 1 | | 2 | | |
| Ex. 12 | 3 | 2 | 15 | 20 | 30 | 30 | | 1.6 | | 0.8 | | |
| Ex. 13 | 5 | 15 | | 50 | 15 | 15 | | | 0.3 | 0.8 | | |
| Ex. 14 | 7 | 13 | | 50 | | 30 | | | 1.6 | 0.8 | | |
| Ex. 15 | 7 | 13 | | 10 | 40 | | 30 | 1.8 | | | 0.4 | |
| Ex. 16 | 4 | 16 | 10 | 40 | | 30 | | | 1.4 | 0.4 | | 0.4 |
| Ex. 17 | 7 | 13 | | 50 | | 30 | | 1.2 | | 0.4 | | |
| Ex. 18 | 7 | 13 | | 50 | | | 30 | | 2 | | 0.8 | |
| Ex. 19 | 7 | 13 | | 50 | | 30 | | 1.8 | | 0.8 | | |
| Ex. 20 | 4 | 6 | | 20 | 70 | | | 2 | | 0.8 | | |
| Comp. Ex. 3 | | | | 50 | | 30 | 20 | 0.3 | | 1 | | |
| Comp. Ex. 4 | | | | 50 | | 30 | 20 | 1.6 | | 0.8 | | |
| Comp. Ex. 5 | | | | 10 | 70 | | 20 | 2 | | 0.8 | | |
| Comp. Ex. 6 | 7 | 13 | | 50 | | 30 | | 0.3 | | | | |
| Comp. Ex. 7 | 7 | 13 | | 50 | | 30 | | 0.3 | | 10 | | |
| Comp. Ex. 8 | 7 | 13 | | 50 | | 30 | | 1.6 | | | | |
| Comp. Ex. 9 | 7 | 13 | | 50 | | 30 | | 1.6 | | 10 | | |
| Comp. Ex. 10 | 33 | 67 | | | | | | 1.6 | | 0.8 | | |
| Comp. Ex. 11 | 7 | 13 | | 50 | | 30 | | | | 0.8 | | |

TABLE 1-continued

| | | | | | | | |
|---|---|---|---|---|---|---|---|
| Comp. Ex. 12 | 7 | 13 | 50 | 30 | 1.6 | 0.8 | |
| Comp. Ex. 13 | 7 | 13 | 50 | 30 | 1.6 | 0.8 | |

| | Powdery component ||||||||
|---|---|---|---|---|---|---|---|---|
| | Component C ||| Component D |||||
| | BPO | PTSNa | PBTEOA | FASG | SE-1 | Si—Zr | Si—Ti | PMMA |
| Ex. 1 | 3.5 | | 0.7 | 160 | 70 | | | |
| Ex. 2 | 3.5 | | 0.7 | 160 | 70 | | | |
| Ex. 3 | 2.3 | 0.7 | | 160 | 70 | | | |
| Ex. 4 | 3.5 | | 1 | | | | | 233 |
| Ex. 5 | 2.3 | 0.7 | | 140 | 93 | | | |
| Ex. 6 | 3.6 | 0.7 | 0.5 | | 93 | | 140 | |
| Ex. 7 | 2.3 | 0.7 | | | 93 | 140 | | |
| Ex. 8 | 2.3 | 0.2 | | | 70 | 163 | | |
| Ex. 9 | 1 | | 0.7 | 163 | | 70 | | |
| Ex. 10 | 2.3 | 0.5 | | | 93 | | 140 | |
| Ex. 11 | 0.7 | 0.7 | | 117 | | 117 | | |
| Ex. 12 | 3.5 | | 4.7 | | | 117 | 117 | |
| Ex. 13 | 3.5 | | 0.7 | 140 | 93 | | | |
| Ex. 14 | 3.5 | | 2.3 | | 70 | 163 | | |
| Ex. 15 | 1.4 | | 0.7 | | 70 | 163 | | |
| Ex. 16 | 3.5 | | 0.7 | 163 | | 70 | | |
| Ex. 17 | 2.3 | 0.5 | | | 70 | 163 | | |
| Ex. 18 | 2.3 | | 2.3 | | 70 | 163 | | |
| Ex. 19 | 2.3 | 0.7 | | | 70 | | 163 | |
| Ex. 20 | 4.6 | | 1 | 47 | | | | 187 |
| Comp. Ex. 3 | 3.5 | | 0.7 | 160 | 70 | | | |
| Comp. Ex. 4 | 2.3 | 0.7 | | 160 | 70 | | | |
| Comp. Ex. 5 | 3.5 | | 1 | | | | | 233 |
| Comp. Ex. 6 | 3.5 | | 0.7 | 160 | 70 | | | |
| Comp. Ex. 7 | 3.5 | | 0.7 | 160 | 70 | | | |
| Comp. Ex. 8 | 2.3 | 0.7 | | 160 | 70 | | | |
| Comp. Ex. 9 | 2.3 | 0.7 | | 160 | 70 | | | |
| Comp. Ex. 10 | 2.3 | 0.7 | | 160 | 70 | | | |
| Comp. Ex. 11 | | | | 160 | 70 | | | |
| Comp. Ex. 12 | 2.3 | 0.7 | | 10 | | | | |
| Comp. Ex. 13 | 2.3 | 0.7 | | 600 | 500 | | | |

TABLE 2

| | Adhesion to tooth/ MPa | Adhesion to enamel/ MPa | Cure start/end time (min) | Removal time (sec) | Color tone b* | Compression strength of cured body/MPa |
|---|---|---|---|---|---|---|
| Ex. 1 | 7.6 | 10.2 | 3.8/6.3 | 180 | 10.1 | 210 |
| Ex. 2 | 7.8 | 10.1 | 5.1/9.5 | 300 | 9.9 | 160 |
| Ex. 3 | 8.2 | 10.3 | 2.3/4.8 | 180 | 10.9 | 190 |
| Ex. 4 | 8.1 | 10.4 | 3.1/5.1 | 160 | 10.1 | 158 |
| Ex. 5 | 7.2 | 12.1 | 3.1/7.5 | 270 | 10.8 | 187 |
| Ex. 6 | 8.8 | 12.4 | 4.2/8.5 | 280 | 10.9 | 195 |
| Ex. 7 | 7.5 | 12.6 | 3.1/4.3 | 100 | 12.1 | 213 |
| Ex. 8 | 8.2 | 11.0 | 3.4/5.1 | 120 | 11.7 | 201 |
| Ex. 9 | 7.8 | 9.8 | 2.5/6.5 | 270 | 10.5 | 181 |
| Ex. 10 | 7.8 | 11.0 | 2.8/6.3 | 240 | 10.6 | 194 |
| Ex. 11 | 7.8 | 10.9 | 3.9/7.6 | 270 | 10.3 | 211 |
| Ex. 12 | 7.1 | 10.5 | 3.1/6.3 | 210 | 10.2 | 187 |
| Ex. 13 | 7.3 | 10.1 | 3.1/6.0 | 210 | 10.5 | 194 |
| Ex. 14 | 8.1 | 10.7 | 3.0/6.5 | 240 | 10.9 | 184 |
| Ex. 15 | 7.9 | 11.2 | 2.7/4.1 | 120 | 11.3 | 198 |
| Ex. 16 | 8.5 | 12.3 | 3.5/6.4 | 210 | 10.6 | 203 |
| Ex. 17 | 8.5 | 12.3 | 3.2/4.7 | 130 | 11.1 | 204 |
| Ex. 18 | 7.3 | 11.5 | 3.3/5.7 | 180 | 10.8 | 205 |
| Ex. 19 | 8.6 | 11.4 | 3.1/6.3 | 210 | 10.9 | 194 |
| Ex. 20 | 7.9 | 11.2 | 3.1/5.0 | 150 | 10.3 | 158 |
| Comp. Ex. 1 | 3.1 | 5.0 | 4.7/5.3 | 50 | 12.8 | 197 |
| Comp. Ex. 2 | 2.7 | 4.4 | 5.8/6.6 | 60 | 14.3 | 201 |
| Comp. Ex. 3 | 2.1 | 4.1 | 3.0/4.1 | 100 | 12.9 | 223 |
| Comp. Ex. 4 | 1.6 | 3.8 | 1.9/3.3 | 120 | 13.9 | 218 |
| Comp. Ex. 5 | 2.8 | 4.9 | 2.1/3.6 | 120 | 12.1 | 152 |
| Comp. Ex. 6 | 7.6 | 10.3 | 2.7/3.1 | <30 | 13.1 | 210 |
| Comp. Ex. 7 | 3.4 | 5.3 | 7.9/15.2 | 450 | 9.1 | 90 |
| Comp. Ex. 8 | 7.6 | 11.0 | 2.3/2.9 | <30 | 13.5 | 186 |
| Comp. Ex. 9 | 2.4 | 4.5 | 8.2/20.2 | 720 | 8.7 | 88 |
| Comp. Ex. 10 | 5.5 | 6.0 | 3.3/4.5 | 90 | 10.1 | 120 |

The invention claimed is:

1. A dental adhesive comprising:

(A) a radically polymerizable acidic phosphoric acid ester and (B) a radically polymerizable monomer other than (A) in such amounts as A:B =5:95 to 80:20 based on the mass, and further comprising, per 100 parts by mass of the total amount of said radically polymerizable monomers (A) and (B):

(C) a chemical polymerization initiator in an amount of 0.05 to 15 parts by mass;

(D) a filler in an amount of 20 to 1000 parts by mass; and (E) a compound represented by the following general formula (1), (1)

wherein R¹ and R² are, independently from each other, hydrogen atoms or alkyl groups with 1 to 3 carbon atoms, in an amount of 0.01 to 5 parts by mass.

2. A dental adhesive according to claim 1, wherein the radically polymerizable acidic phosphoric acid ester (A) is represented by the following general formula (2), (2)

wherein $R^3$ is a hydrogen atom or a methyl group, $R^4$ is an organic residue having a valency of 2 to 6 and 1 to 30 carbon atoms, W is an oxygen atom, a sulfur atom or NH, Z is —O—P(=O)(OH)$_2$ or —O—P(=O)(OH)(OR$^5$), wherein $R^5$ is an alkyl group having 1 to 10 carbon atoms on the main chain or an aryl group having 6 to 14 carbon atoms constituting a ring, said alkyl group or aryl group may be substituted with a halogen atom, a hydroxyl group, a cyano group, a nitro group, an alkyl group having 1 to 5 carbon atoms, an alkenyl group having 2 to 5 carbon atoms, an alkinyl group having 2 to 5 carbon atoms, an alkoxyl group having 1 to 5 carbon atoms, an acyl group having 2 to 5 carbon atoms or an acyloxy group having 2 to 5 carbon atoms, or may further be substituted with a plurality of the same or different substituents, m and n are, independently from each other, integers of 1 to 5, and m+n is in agreement with the valency of $R^4$.

3. A dental adhesive according to claim 1, wherein the radically polymerizable acidic phosphoric acid ester (A) is represented by the following general formula (3), (3)

wherein $R^{3'}$ and $R^{3''}$ are, independently from each other, hydrogen atoms or methyl groups, $R^{4'}$ and $R^{4''}$ are, independently from each other, organic residues having a valency of 2 to 6 and 1 to 30 carbon atoms, W' and W" are, independently, from each other, oxygen atoms, sulfur atoms or NH, m' and m" are, independently from each other, integers of 1 to 5, (m'+1) is in agreement with a valency of $R^{4'}$, and (m"+1) is in agreement with a valency of $R^{4''}$.

4. A dental adhesive according to claim 1, wherein the radically polymerizable monomer (B) other than (A) includes a radically polymerizable monomer of a polyfunctional (meth)acrylic acid ester.

5. A dental adhesive according to claim 1, wherein the radically polymerizable monomer (B) other than (A) comprises a radically polymerizable monomer of a polyfunctional (meth)acrylic acid ester and a radically polymerizable monomer of a monofunctional (meth)acrylic acid ester.

6. A dental adhesive according to claim 1, wherein said chemical polymerization initiator (C) comprises a combination of an organic peroxide and an amine.

7. A dental adhesive according to claim 1, wherein the filler (D) is a fluoroaluminosilicate glass.

8. A dental adhesive composition according to claim 1, wherein the compound represented by the above general formula (1) is a 2,4-diphenyl-4-methyl-1-pentene.

9. A dental adhesive according to claim 1, wherein the time from the start of curing to the end of curing per 0.2 g thereof set at 37° C. as measured by a dental rheometer is from 1.0 to 5.0 minutes.

* * * * *